(12) United States Patent
Lin et al.

(10) Patent No.: US 9,606,350 B2
(45) Date of Patent: Mar. 28, 2017

(54) FORWARD SCANNING OPTICAL PROBES

(71) Applicant: Novartis AG, Basel (CH)

(72) Inventors: Dean Y. Lin, Chino Hills, CA (US);
Kambiz Parto, Laguna Hills, CA (US);
Edouard G. Schmidtlin, Studio City, CA (US); Barry L. Wheatley, Oceanside, CA (US)

(73) Assignee: Novartis AG, Lichtstrasse, Basel (CH)

( * ) Notice: Subject to any disclaimer, the term of this patent is extended or adjusted under 35 U.S.C. 154(b) by 0 days.

(21) Appl. No.: 13/874,738

(22) Filed: May 1, 2013

(65) Prior Publication Data
US 2014/0327947 A1 Nov. 6, 2014

(51) Int. Cl.
| | |
|---|---|
| *G02B 26/10* | (2006.01) |
| *G02B 26/08* | (2006.01) |
| *A61B 5/00* | (2006.01) |
| *A61B 1/00* | (2006.01) |
| *A61B 18/22* | (2006.01) |
| *G02B 6/26* | (2006.01) |
| *A61B 18/20* | (2006.01) |

(52) U.S. Cl.
CPC ........ *G02B 26/103* (2013.01); *A61B 1/00172* (2013.01); *A61B 5/0062* (2013.01); *A61B 5/0084* (2013.01); *A61B 18/22* (2013.01); *G02B 26/0875* (2013.01); *A61B 5/0066* (2013.01); *A61B 2018/209* (2013.01); *A61B 2018/2095* (2013.01); *G02B 6/262* (2013.01)

(58) Field of Classification Search
CPC .... G02B 26/103; G02B 26/10; G02B 26/101; G02B 26/0875; G02B 6/26; A61B 1/07; A61B 1/00096; A61B 1/00101; A61B 1/00165; A61B 1/001652; A61B 1/00172; A61B 5/0062; A61B 5/0066; A61B 5/0084; A61B 18/22; A61B 2018/209; A61B 2018/2095
USPC ......... 359/201.1, 202.1, 203.1, 209.1–210.2; 600/160, 162–164, 167, 168, 171, 600/173–177, 182
See application file for complete search history.

(56) References Cited

U.S. PATENT DOCUMENTS

| | | |
|---|---|---|
| 6,236,787 B1 | 5/2001 | Laughlin |
| 6,239,895 B1 | 5/2001 | Keeney et al. |
| 6,485,413 B1 | 11/2002 | Boppart et al. |
| 7,261,687 B2 | 8/2007 | Yang |

(Continued)

OTHER PUBLICATIONS

Yaqoob, Z., et al., "Methods and application areas of endoscopic optical coherence tomography", J. of Biomedical Optics, Nov./Dec. 2006, vol. 11(6), pp. 063001-1-19.

*Primary Examiner* — Thomas K Pham
*Assistant Examiner* — Marin Pichler

(57) ABSTRACT

In certain embodiments, a scanning system includes optical elements and a movement system. The optical elements include an optical fiber and a gradient-index (GRIN) lens. The optical fiber has a fiber axis that extends to an imaginary fiber axis, and is configured to transmit a light ray. The GRIN lens has a GRIN perimeter and a GRIN lens optical axis, and is configured to refract the light ray. The movement system moves a first optical element relative to a second optical element in a closed path such that the GRIN lens optical axis substantially aligns with the imaginary fiber axis at at least one point of the path and the GRIN perimeter intersects the imaginary fiber axis at at least two points of the path.

4 Claims, 3 Drawing Sheets

(56) References Cited

U.S. PATENT DOCUMENTS

| | | |
|---|---|---|
| 7,364,543 B2 | 4/2008 | Yang et al. |
| 2005/0234345 A1 | 10/2005 | Yang |
| 2006/0271082 A1 | 11/2006 | Kirchhevel et al. |
| 2007/0066871 A1* | 3/2007 | Yang et al. ................ 600/173 |
| 2008/0177139 A1* | 7/2008 | Courtney et al. ........... 600/109 |
| 2011/0028967 A1* | 2/2011 | Rollins et al. ................ 606/41 |
| 2012/0190921 A1* | 7/2012 | Yadlowsky et al. ......... 600/106 |
| 2012/0310042 A1* | 12/2012 | Joos et al. .................. 600/108 |

* cited by examiner

FORWARD SCANNING OPTICAL PROBES

TECHNICAL FIELD

The present disclosure relates generally to surgical devices, and more particularly to forward scanning optical probes.

BACKGROUND

Optical imaging techniques generate images of targets such as portions of a body, e.g., the interior of an eye. Examples of such techniques include interferometric imaging (e.g., optical coherence tomography (OCT)), spectroscopic imaging (e.g., fluorescence), Raman imaging, diffuse-wave optical imaging, and two-photon imaging techniques. Certain techniques, such as the interferometric imaging techniques, use a scanning system to scan a light ray across the target to image the target. Optical elements such as mirrors and lenses may be used to move the light ray.

BRIEF SUMMARY

In certain embodiments, a scanning system includes optical elements and a movement system. The optical elements include an optical fiber and a gradient-index (GRIN) lens. The optical fiber has a fiber axis that extends to an imaginary fiber axis, and is configured to transmit a light ray. The GRIN lens has a GRIN perimeter and a GRIN lens optical axis, and is configured to refract the light ray. The movement system moves a first optical element relative to a second optical element in a closed path such that the GRIN lens optical axis substantially aligns with the imaginary fiber axis at at least one point of the path and the GRIN perimeter intersects the imaginary fiber axis at at least two points of the path.

BRIEF DESCRIPTION OF THE DRAWINGS

Exemplary embodiments of the present disclosure will now be described by way of example in greater detail with reference to the attached figures, in which.

DESCRIPTION OF EXAMPLE EMBODIMENTS

Figure 1:
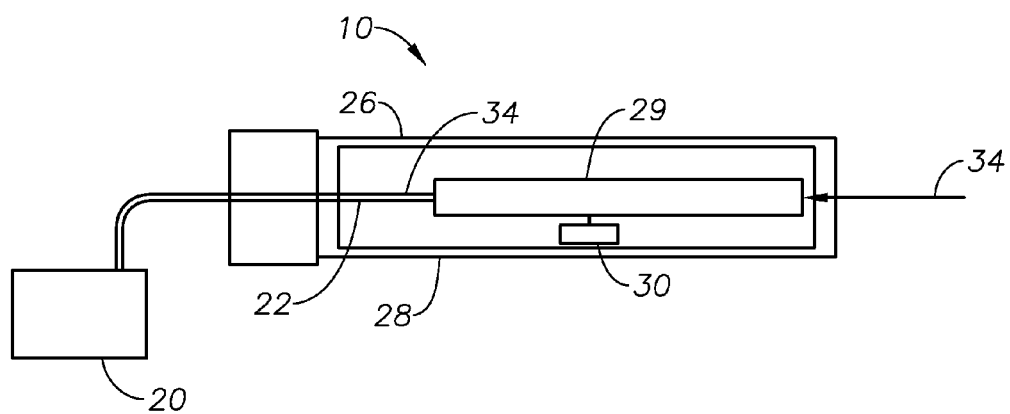
FIG. 1 illustrates an example of a probe with a scanning system that scans according to certain embodiments.

Referring now to the description and drawings, example embodiments of the disclosed apparatuses, systems, and methods are shown in detail. The description and drawings are not intended to be exhaustive or otherwise limit or restrict the claims to the specific embodiments shown in the drawings and disclosed in the description. Although the drawings represent possible embodiments, the drawings are not necessarily to scale and certain features may be exaggerated, removed, or partially sectioned to better illustrate the embodiments.

FIG. 1 illustrates an example of a probe 10 with a scanning system 28 that scans according to certain embodiments. In the illustrated embodiment, probe 10 includes a light source 20 and a housing 26 coupled as shown. A scanning system 28 is disposed within housing 26. Scanning system 28 include one or more optical elements 29 (including optical fiber 22) and a movement system 30. In an example of operation, light source 20 provides a light ray 34 that is transmitted through optical fiber 22 to other optical elements 29. Movement system 30 moves one or more of the optical elements 29 in order to output a scanning light ray 34.

Light source 20 may be a laser that generates light. Examples of laser include gas lasers, dye lasers, metal vapor lasers, solid state lasers, semiconductor lasers, fiber lasers, and supercontinuum lasers. The light may have any suitable spectral range, e.g., 750 nanometers (nm) to 950 nm.

Housing 26 (e.g., a cannula) may have any suitable shape and size. The housing may have a tubular (or cylindrical) shape with any suitable length and diameter, such as a length in the range of one to two inches, an outer diameter (OD) in the range of 0.05 to 0.02 inches, and an inner diameter (ID) in the range of 0.04 to 0.01 inches (but of course can be larger or smaller). For cannulas, the size may depend on the gauge (ga) of the cannula. For example, 20 ga cannulas may be approximately 0.0365" in OD and 0.031" in ID; 23 ga cannulas may be approximately 0.0255" in OD and 0.021" in ID; and 25 ga cannulas may be approximately 0.0205" in OD and 0.0156" in ID. This disclosure contemplates even smaller (higher gauge) cannulas.

Scanning system 28 receives light ray 34 and scans light ray 34 to output a scanning light ray 34. Scanning system 28 includes one or more optical elements 29 and movement system 30. An optical element 29 may be any suitable optical element that can reflect, refract, and/or diffract light. Examples of optical elements include optical fibers (e.g., optical fiber 22), lenses (e.g., a gradient-index (GRIN) lens), prisms, mirrors, or other elements that can reflect, refract, and/or diffract light. An optical element 29 has an optical axis. For example, optical fiber 22 has a fiber axis. To aid in the description of relative movement among optical elements 29, the optical axis of an optical element 29 may be regarded as extending past the physical boundaries of the element as an imaginary axis. For example, the fiber axis may be described as extending to an imaginary fiber axis. In certain embodiments, an optical axis of an optical element 29 may have specific features. For example, light rays passing through the optical axis of a GRIN lens may be output with zero degrees of refraction.

Optical fiber is generally a transparent fiber that operates as a waveguide to transmit light from a laser source 20. Optical fiber 22 may include an optically transmissive fiber core surrounded by a cladding material having a generally low index of refraction relative to the fiber core. Optical fiber 22 may comprise any suitable material, e.g., glass and/or plastic. Optical fiber 22 may include additional layers depending on the requirements of a particular application. Optical fiber 22 has a fiber axis that is typically the optical axis of the fiber core.

Movement system 30 may move an optical element 29 in any suitable manner. For example, the optical element may be translated, rotated about an axis, or orbited around an axis. A translational movement is generally linear motion. A rotational movement of an object is movement about an axis of the object. An orbital movement of an object is movement around an axis external to the object. Movement system 30 may move an optical element in a closed path in which the starting point of the path substantially coincides with the ending point.

Movement system 30 may move an optical element 29 using any suitable movement mechanism. As an example, an electric motor (e.g., a piezoelectric motor) may be used to move an optical element 29. As another example, electrostatic plates may be used to move an optical element 29 treated with a metalized material. As yet another example, an optical element 29 may be moved with a pneumatic device and/or one or more springs. In certain embodiments, movement system 30 may be controlled by one or more computer readable media encoded with a computer program.

Figure 4:
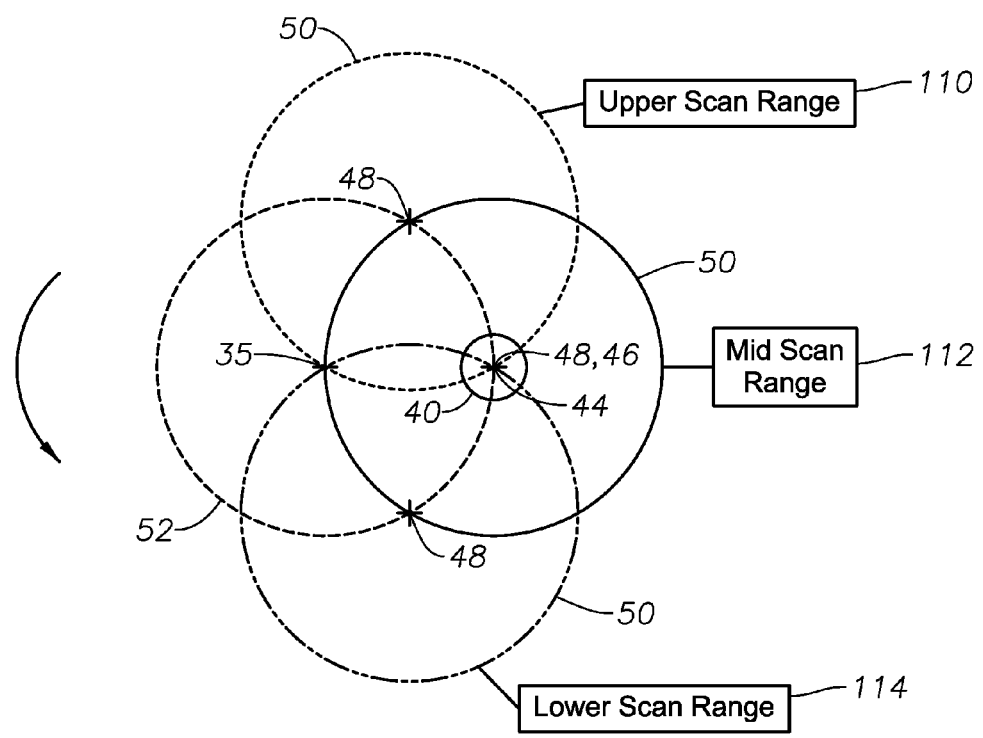
FIG. 4 illustrates an example of a method of scanning that a scanning system may implement according to certain embodiments.
Figure 2A:
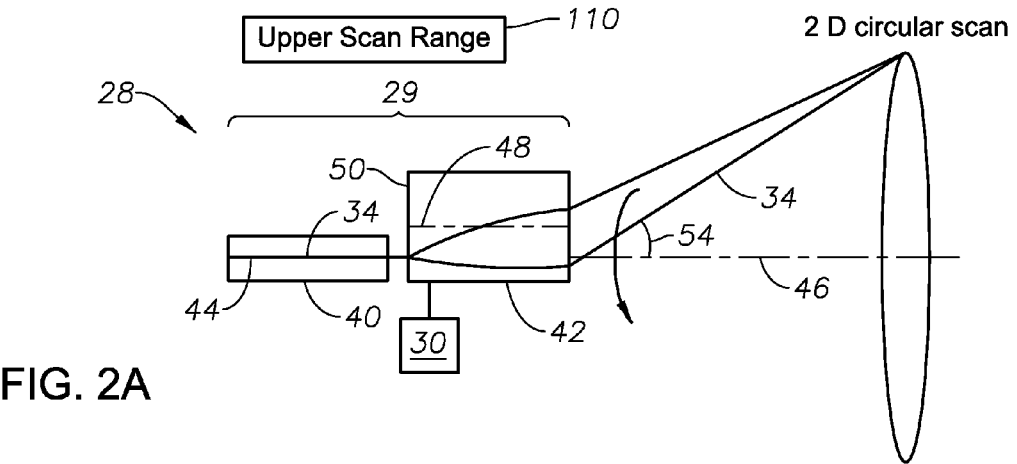
FIGS. 2A-2C illustrate an example of a scanning system that scans according to certain embodiments.
Figure 2B:
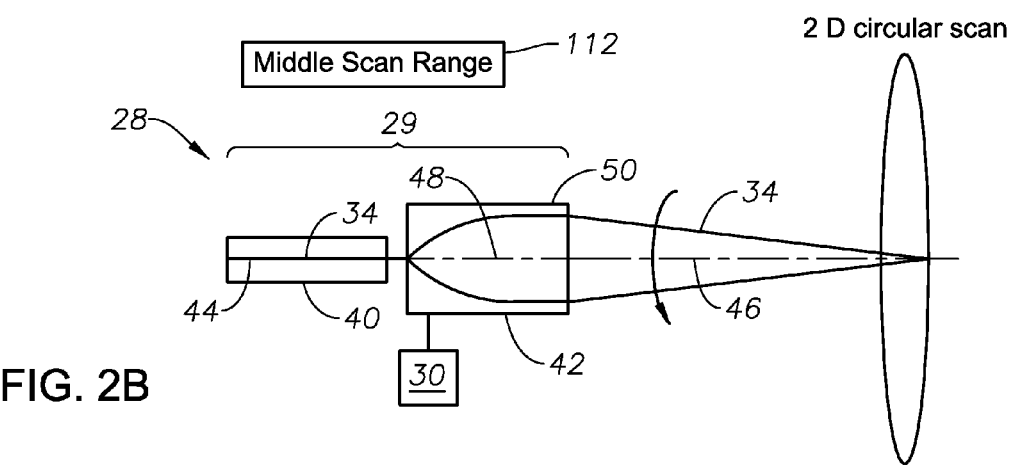
Figure 2C:
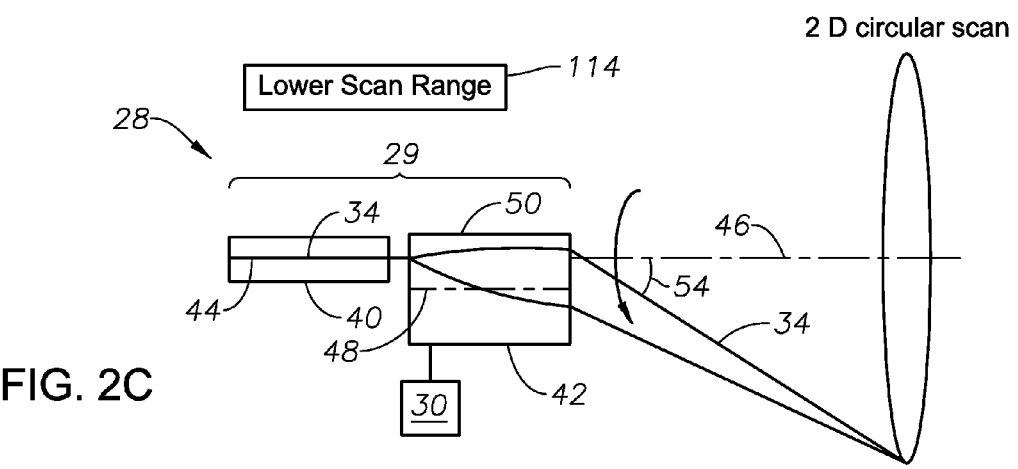

FIGS. 2A-2C and 3A-3D illustrate an example of a scanning system 28 and a movement system 30 that may implement the example of a scanning method illustrated in FIG. 4 according to certain embodiments. In the illustrated example, scanning system 28 includes optical elements 29 and movement system 30. Optical elements 29 include optical fiber 40 and GRIN lens 42. Optical fiber 40 transmits light ray 34 to GRIN lens 42. Optical fiber 40 has a fiber axis 44 that extends to an imaginary fiber axis 46. GRIN lens 42 has a GRIN lens optical axis 48 and a GRIN perimeter 50.

Movement system 30 is coupled to at least one of the optical elements 29 and moves a first optical element 29 relative to a second optical element 29 in a closed path 52 to yield a light ray that scans a 2-dimensional pattern on a target. Movement system 30 may move optical fiber 40 and/or GRIN lens 42. For example, movement system 30 may move GRIN lens 42 relative to optical fiber 40 and/or move optical fiber 40 relative to GRIN lens 42.

In the example of FIGS. 3A-3D, movement system 30 includes a cylinder 33 that rotates about a cylinder axis 35. GRIN lens 42 is disposed within cylinder 33 such that cylinder axis 35 is substantially parallel to GRIN lens optical axis 48, but separated from GRIN lens optical axis 48. Cylinder 33 may have any suitable size. For example, cylinder 33 may be approximately the same length as GRIN lens 42 and have a radius 37 that is larger than, e.g., approximately two times larger than, the radius 39 of GRIN lens 42. In certain embodiments, GRIN lens 42 is coupled to the inner surface of cylinder 33.

Closed path 52 may have any suitable shape, e.g., circular or elliptical. In addition, GRIN lens 42 may be moved along closed path 52 at any suitable speed. In certain examples, GRIN lens 42 may be moved at a constant speed, which may be expressed as a number of paths per unit of time, i.e., path/time. The path/time may have any suitable value, e.g., a value in the range of 10 hertz (Hz) to 100 Hz.

According to certain scanning methods, GRIN lens optical axis 48 substantially aligns with (e.g., coincides with) imaginary fiber axis 46 at at least one point of the path and GRIN perimeter 50 intersects the imaginary fiber axis 46 at at least two points of path 52. For example, in a particular scanning method, the method starts as movement of GRIN lens 42 is initiated relative to optical fiber 40 along closed path 52. At step 110 (shown in FIGS. 2A, 3A, and 4), GRIN lens 42 is at the upper scan range where a first point of GRIN perimeter 50 intersects imaginary fiber axis 46. At this point, light ray 34 hits GRIN lens 42 at a point away from GRIN lens optical axis 48, near or at GRIN lens perimeter 50. The off-center contact yields light ray 34 that exits the distal surface of GRIN lens 42 at an angle 54. In general, angle 54 decreases to zero as light ray 34 approaches GRIN lens optical axis 48, and increases as light ray 34 approaches GRIN perimeter 50.

Figure 3A:
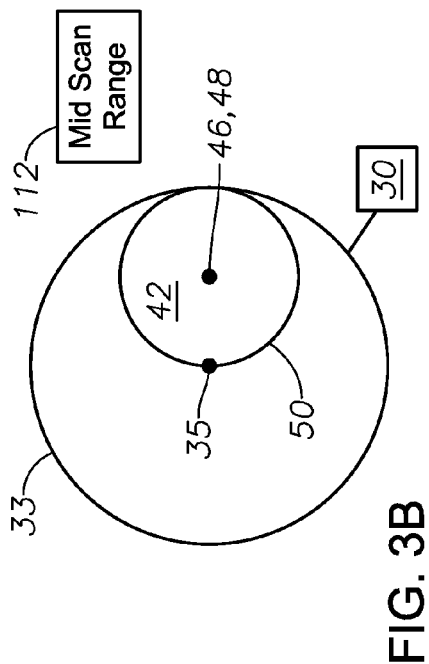
FIGS. 3A-3D illustrate an example of a movement system that scans according to certain embodiments.
Figure 3B:
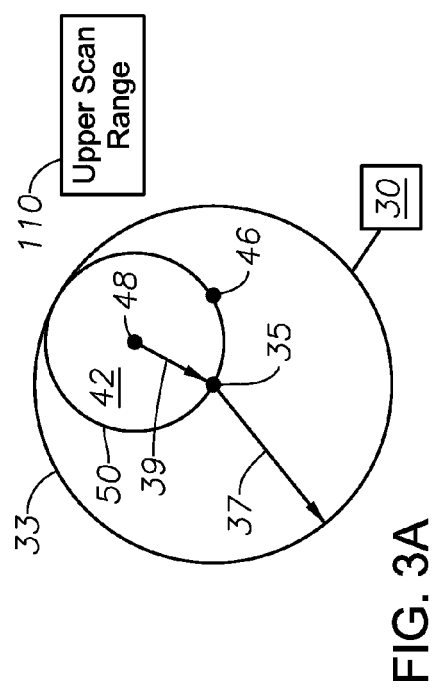
Figure 3C:
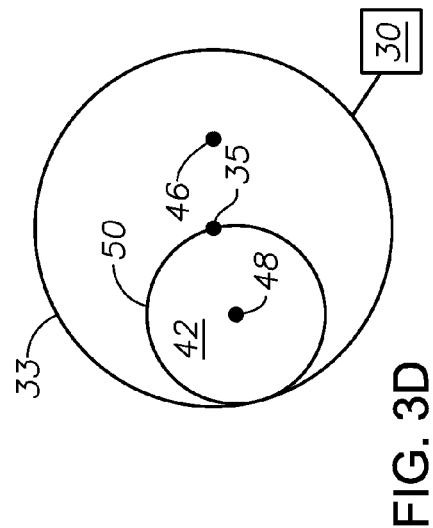
Figure 3D:
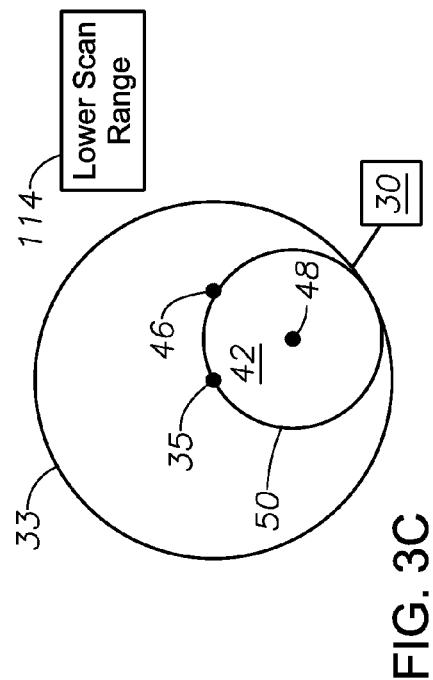

At step 112 (shown in FIGS. 2B, 3B, and 4), GRIN lens 42 is at the middle scan range where GRIN lens optical axis 48 is aligned with imaginary fiber axis 46. Light ray 34 travels along GRIN lens optical axis 48. At step 114 (shown in FIGS. 2C, 3C, and 4), GRIN lens 42 is at the upper scan range where a second point of GRIN perimeter 50 intersects imaginary fiber axis 46. At this point, light ray 34 hits GRIN lens 42 away from GRIN lens optical axis 48, near or at GRIN lens perimeter 50. The off-center contact yields light ray 34 that exits the distal surface of GRIN lens 42 at an angle 54. Angle 54 at step 114 is opposite to angle 54 at step 110. FIG. 3D illustrates a portion of closed path 52 at which light ray 34 does not pass through GRIN lens 42.

In this above example, GRIN lens 42 moves relative to optical fiber 40. In other examples, optical fiber 40 may move relative to GRIN lens 42 or both GRIN lens 42 and optical fiber 40 may move.

A component (e.g., scanning system 28 and/or movement system 30) of the systems and apparatuses disclosed herein may include an interface, logic, memory, and/or other suitable element, any of which may include hardware and/or software. An interface can receive input, send output, process the input and/or output, and/or perform other suitable operations. Logic can perform the operations of a component, for example, execute instructions to generate output from input. Logic may be encoded in memory and may perform operations when executed by a computer. Logic may be a processor, such as one or more computers, one or more microprocessors, one or more applications, and/or other logic. A memory can store information and may comprise one or more tangible, computer-readable, and/or computer-executable storage medium. Examples of memory include computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server), and/or other computer-readable media.

In particular embodiments, operations of the embodiments (e.g., control of scanning of light ray 34) may be performed by one or more computer readable media encoded with a computer program, software, computer executable instructions, and/or instructions capable of being executed by a computer. In particular embodiments, the operations may be performed by one or more computer readable media storing, embodied with, and/or encoded with a computer program and/or having a stored and/or an encoded computer program.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein. The methods may include more, fewer, or other steps, and the steps may be performed in any suitable order.

Other modifications are possible without departing from the scope of the invention. For example, the description illustrates embodiments in particular practical applications, yet other applications will be apparent to those skilled in the art. In addition, future developments will occur in the arts discussed herein, and the disclosed systems, apparatuses, and methods will be utilized with such future developments.

The scope of the invention should not be determined with reference to the description. In accordance with patent statutes, the description explains and illustrates the principles and modes of operation of the invention using exemplary embodiments. The description enables others skilled in the art to utilize the systems, apparatuses, and methods in various embodiments and with various modifications, but should not be used to determine the scope of the invention.

The scope of the invention should be determined with reference to the claims and the full scope of equivalents to which the claims are entitled. All claims terms should be given their broadest reasonable constructions and their ordinary meanings as understood by those skilled in the art, unless an explicit indication to the contrary is made herein. For example, use of the singular articles such as "a," "the," etc. should be read to recite one or more of the indicated elements, unless a claim recites an explicit limitation to the contrary. As another example, "each" refers to each member of a set or each member of a subset of a set, where a set may include zero, one, or more than one element. In sum, the invention is capable of modification, and the scope of the invention should be determined, not with reference to the description, but with reference to the claims and their full scope of equivalents.

What is claimed is:

1. A scanning system comprising:
    a plurality of optical elements comprising:
        an optical fiber having a fiber axis that is the optical axis of the fiber, the optical fiber configured to transmit a light ray, the fiber axis extending to an imaginary fiber axis that is in the same direction as the fiber axis; and
        a gradient-index (GRIN) lens having a GRIN perimeter and a GRIN lens optical axis, the GRIN lens configured to receive the light ray from the optical fiber and refract the light ray; and
    a movement system comprising a cylinder having a cylinder axis, the GRIN lens disposed in an offset manner within the cylinder such that the cylinder axis is substantially parallel to but separated from the GRIN optical lens axis, the movement system configured to rotate the cylinder to move the offset GRIN lens separately from the optical fiber in a substantially circular closed path such that the GRIN lens does not rotate about the GRIN lens optical axis, but instead the GRIN lens optical axis substantially aligns with the imaginary fiber axis at at least one point of the path and the GRIN perimeter intersects the imaginary fiber axis at at least two points of the path.

2. The scanning system of claim 1, the GRIN lens moved at a path/time in the range of 10 Hz to 100 Hz.

3. A scanning method comprising:
    transmitting a light ray through an optical fiber having a fiber axis that is the optical axis of the fiber, the fiber axis extending to an imaginary fiber axis that is in the same direction as the fiber axis;
    initiating rotation of a cylinder having a cylinder axis, a gradient-index (GRIN) lens disposed within the cylinder in an offset manner such that the cylinder axis is substantially parallel to but separated from the GRIN optical lens axis, the GRIN lens having a GRIN perimeter and a GRIN lens optical axis, the GRIN lens configured to receive the light ray from the optical fiber and refract the light ray;
    moving the offset GRIN lens along a substantially circular closed path relative to and separately from the optical fiber such that the GRIN lens does not rotate about the GRIN lens optical axis;
    moving the GRIN lens such that a first point of the GRIN perimeter intersects the imaginary fiber axis;
    moving the GRIN lens such that the GRIN lens optical axis substantially aligns with the imaginary fiber axis; and
    moving the GRIN lens such that a second point of the GRIN perimeter intersects the imaginary fiber axis.

4. The scanning method of claim 3, the GRIN lens moved at a path/time in the range of 10 Hz to 100 Hz.

\* \* \* \* \*